United States Patent
Jingu et al.

(10) Patent No.: US 10,024,789 B2
(45) Date of Patent: Jul. 17, 2018

(54) MEASUREMENT METHOD USING DIFFERENTIAL REFRACTOMETER, DIFFERENTIAL REFRACTOMETER USING THE MEASUREMENT METHOD, AND LIQUID CHROMATOGRAPH

(71) Applicant: SHIMADZU CORPORATION, Kyoto-shi, Kyoto (JP)

(72) Inventors: Kumiko Jingu, Kyoto (JP); Masanori Fujiwara, Kyoto (JP); Masami Tomita, Kyoto (JP); Yutaka Kono, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 216 days.

(21) Appl. No.: 15/115,362

(22) PCT Filed: Feb. 7, 2014

(86) PCT No.: PCT/JP2014/052954
§ 371 (c)(1),
(2) Date: Jul. 29, 2016

(87) PCT Pub. No.: WO2015/118668
PCT Pub. Date: Aug. 13, 2015

(65) Prior Publication Data
US 2017/0010213 A1    Jan. 12, 2017

(51) Int. Cl.
*G01N 21/41*    (2006.01)
*G01N 30/74*    (2006.01)

(52) U.S. Cl.
CPC ......... *G01N 21/4133* (2013.01); *G01N 30/74* (2013.01); *G01N 2021/4146* (2013.01)

(58) Field of Classification Search
CPC ....... G01N 21/4133; G01N 2021/4146; G01N 30/74
See application file for complete search history.

(56) References Cited

U.S. PATENT DOCUMENTS 4,798,081 A  *  1/1989  Hazlitt ................. G01N 11/08
                                                        73/53.01
5,011,608 A       4/1991  Damjanovic
(Continued)

FOREIGN PATENT DOCUMENTS

JP          11-23555 A        1/1999
JP          2006-84457 A     3/2006
(Continued)

OTHER PUBLICATIONS

Dolan, John W. "Avoiding Refractive Index Detector Problems" LCGC North America, vol. 30, Issue 12, pp. 1032-1037, Dec. 1, 2012.*

(Continued)

*Primary Examiner* — Paul West
(74) *Attorney, Agent, or Firm* — Westerman, Hattori, Daniels & Adrian, LLP

(57) ABSTRACT

A differential refractometer including a measurement section for measuring the diffractive index difference between a sample cell and a reference cell by radiating light on a measurement cell and detecting light which has sequentially passed through the sample cell and the reference cell includes a mobile phase supply section for delivering a mobile phase in a sample introduction channel that is connected to the sample cell. The mobile phase supply section includes a mobile phase container for containing the mobile phase. The inside of the mobile phase container is continuously stirred by a stirring mechanism, and the composition of the mobile phase inside the mobile phase container is made uniform.

10 Claims, 8 Drawing Sheets

(56) References Cited

U.S. PATENT DOCUMENTS

2005/0168726 A1   8/2005   Larkin et al.
2005/0168733 A1   8/2005   Larkin
2010/0096380 A1   4/2010   Satoh et al.

FOREIGN PATENT DOCUMENTS

JP    2006-105998 A    4/2006
JP    2012-68024 A     4/2012
WO    2008/102872 A1   8/2008

OTHER PUBLICATIONS

International Search Report dated May 13, 2014, issued in counterpart International Application No. PCT/JP2014/052954 (2 pages).

* cited by examiner

MEASUREMENT METHOD USING DIFFERENTIAL REFRACTOMETER, DIFFERENTIAL REFRACTOMETER USING THE MEASUREMENT METHOD, AND LIQUID CHROMATOGRAPH

TECHNICAL FIELD

The present invention relates to a measurement method using a differential refractometer that is used as a detector of an analytical device such as a liquid chromatograph, a differential refractometer using the measurement method, and a liquid chromatograph.

BACKGROUND ART

A differential refractometer includes a sample cell through which a solution containing a sample is to pass, and a reference cell for a reference solution. These cells are arranged with a light transmissive partition in between. Measurement light from a light source is to sequentially pass through the reference cell and the sample cell. Measurement light is made to diagonally enter the partition between the cells, and the position of the optical axis of light which has passed through both cells is detected by a detector (see Patent Document 1).

The position of the optical axis of light passed through both cells varies depending on the refractive index difference between the reference cell and the sample cell. Since the refractive index of the reference cell is constant, the refractive index difference between the reference cell and the sample cell is changed according to the concentration of the sample solution. Accordingly, by measuring the amount of displacement of the position of the optical axis of light passed through the reference cell and the sample cell, the amount of change in the refractive index of the sample solution may be determined, and the concentration of a component in the sample solution may be determined from the amount of change in the refractive index of the sample solution.

PRIOR ART DOCUMENTS

Patent Documents

Patent Document 1: Japanese Patent Laid-open Publication No. 2012-68024

SUMMARY OF THE INVENTION

Problems to be Solved by the Invention

It is known that the refractive index of a sample cell is greatly influenced by the composition of a mobile phase flowing through the sample cell and the temperature, thereby causing occurrence of undulation or a great drift in the baseline of a detection signal.

When undulation occurs in the baseline of a detection signal during measurement of a sample, the peak area cannot be accurately calculated, and the reliability of the quantitative value of concentration of a component that is calculated is reduced. However, conventionally, no measures were taken to actively suppress undulation occurring in a detection signal.

Furthermore, when the refractive index is changed, the direction of a drift in the baseline of a detection signal may be changed, thereby affecting processing of a waveform of a chromatogram. However, conventionally, no means were taken to actively control a drift in the baseline of a detection signal.

Accordingly, the present invention has its object to enable active control of undulation or a drift in the baseline of a detection signal of a differential refractometer.

Solutions to the Problems

A measurement method according to the present invention is a measurement method that uses a differential refractometer including a sample cell through which a sample solution is to pass, a reference cell for a reference solution, and an optical system configured to radiate light that is sequentially transmitted through both the sample cell and the reference cell and to detect transmitted light by a photodetector, the differential refractometer being for measuring a refractive index difference between the sample cell and the reference cell by detecting displacement of light which has been transmitted through the sample cell and the reference cell.

A first method of the measurement methods according to the present invention includes supplying a mobile phase to the sample cell, continuously stirring inside of a mobile phase container containing the mobile phase, injecting a sample into a channel through which the mobile phase is flowing radiating light on the sample cell and the reference cell and detecting transmitted light by the photodetector, and determining the refractive index difference between the sample cell and the reference cell based on a detection signal of the photodetector.

The present inventors have found that the concentrations of oxides and impurities and the dissolved oxygen concentration in a mobile phase for introducing a sample into a sample cell are sometimes not uniform inside a mobile phase container storing the mobile phase, and the composition of the mobile phase flowing through the sample cell is thereby temporally changed, and that this is one cause for occurrence of undulation in a detection signal. The first method described above is based on such findings.

A second method of the measurement methods according to the present invention includes supplying a mobile phase to the sample cell, degassing the mobile phase to be supplied to the sample cell, calculating an amount of drift in a baseline of a detection signal of the photodetector before measurement of a sample is started, adjusting a degree of degassing of the mobile phase so that the calculated amount of drift falls within a predetermined range, injecting a sample into a channel through which the mobile phase is flowing, after adjustment of the degree of degassing of the mobile phase, radiating light on the sample cell and the reference cell and detecting transmitted light by the photodetector, and determining the refractive index difference between the sample cell and the reference cell based on a detection signal of the photodetector.

The present inventors have found that the direction of a drift and the amount of the drift in the baseline of a detection signal of the differential refractometer are changed by changing the amount of dissolved oxygen in the mobile phase flowing through the sample cell. The second method described above is based on such a finding.

Degassing of the mobile phase may be performed by supplying a degassing gas to a mobile phase container containing the mobile phase. In this case, change of the degree of degassing of the mobile phase is performed by adjusting an amount of supply of the degassing gas to the mobile phase container.

In the second method described above, in a case where a refractive index of the sample cell is given as K1 and a refractive index of the reference cell is given as K2, a direction regarding a drift in a baseline of a detection signal of increase in a refractive index difference (K1−K2) between the sample cell and the reference cell is given as a positive direction, and the direction of reduction in the refractive index difference (K1−K2) between the sample cell and the reference cell is given as a negative direction. In this case, the amount of supply of the degassing gas is increased to increase the amount of drift in the baseline of the detection signal, and the amount of supply of the degassing gas is reduced to reduce the amount of drift in the baseline of the detection signal.

The refractive index of the sample cell changes according to the dissolved oxygen concentration in the mobile phase flowing through the sample cell, and the refractive index of the sample cell is increased as the dissolved oxygen concentration in the mobile phase is reduced compared to the dissolved oxygen concentration in a reference solution in the reference cell. Accordingly, by increasing the amount of supply of the degassing gas to the mobile phase container, the dissolved oxygen concentration in the mobile phase is reduced, the refractive index of the sample cell is increased, and the amount of drift in the baseline of the detection signal is increased. On the other hand, by reducing the amount of supply of the degassing gas to the mobile phase container, the dissolved oxygen concentration in the mobile phase is increased, the refractive index of the sample cell is reduced, and the amount of drift in the baseline of the detection signal is reduced.

A first differential refractometer according to the present invention is configured to perform the first method described above. Specifically, the first differential refractometer includes a measurement cell including a sample cell through which a sample solution is to pass and a reference cell for a reference solution, a sample introduction channel, connected to the sample cell, for introducing a sample into the sample cell together with a mobile phase, a measurement section including a light source for radiating light toward the measurement cell and a photodetector for detecting light which has passed through the sample cell and the reference cell, a mobile phase supply section, including a mobile phase container for containing a mobile phase, for supplying the mobile phase to the sample cell through the sample introduction channel, and a stirring mechanism for continuously stirring inside of the mobile phase container.

As an example of the stirring mechanism, a magnetic stirrer may be cited. A magnetic stirrer remotely drives a stirrer disposed inside a container by magnetic force, and may stir the solution contained in a closed container. Accordingly, this is suitable to be used as the stirring mechanism of the present invention.

A second differential refractometer according to the present invention is configured to perform the second method described above. Specifically, the second differential refractometer includes a measurement cell including a sample cell through which a sample solution is to pass and a reference cell for a reference solution, a sample introduction channel, connected to the sample cell, for introducing a sample into the sample cell together with a mobile phase, a measurement section including a light source for radiating light toward the measurement cell and a photodetector for detecting light which has passed through the sample cell and the reference cell, a mobile phase supply section, including a mobile phase container for containing a mobile phase, for supplying the mobile phase to the sample cell through the sample introduction channel, a degassing device for degassing the mobile phase inside the mobile phase container, and a control section for capturing a detection signal obtained by the photodetector from the measurement section and for controlling operation of the degassing device based on the detection signal, where the control section includes drift amount setting means for setting a target range of an amount of drift in a baseline of the detection signal of the photodetector, drift amount calculation means for calculating the amount of drift in the baseline of the detection signal before measurement of a sample is performed, and degassing degree control means for adjusting a degree of degassing of the mobile phase by the degassing device before measurement of the sample is performed, in such a way that the amount of drift calculated by the drift amount calculation means falls within the target range set by the drift amount setting means.

An example of the degassing device is a degassing gas supply section including a supply source for supplying a degassing gas into the mobile phase container, and an adjustment mechanism for variably adjusting an amount of supply.

As an example of the degassing gas, helium gas may be cited.

According to the second differential refractometer described above, in a case where a refractive index of the sample cell is given as K1 and a refractive index of the reference cell is given as K2, a direction regarding a drift in a baseline of a detection signal of increase in a refractive index difference (K1−K2) between the sample cell and the reference cell is given as a positive direction, and the direction of reduction in the refractive index difference (K1−K2) between the sample cell and the reference cell is given as a negative direction. In this case, the degassing degree control means are preferably configured to increase the degree of degassing of the mobile phase if the amount of drift calculated by the drift amount calculation means is lower than the target range, and to reduce the degree of degassing of the mobile phase if the amount of drift calculated by the drift amount calculation means is higher than the target range.

A liquid chromatograph according to the present invention includes a differential refractometer according to the present invention, a sample introduction section for introducing a sample into a sample introduction channel of the differential refractometer, an analytical column for separating a sample into components, provided on the sample introduction channel, on an upstream side of the differential refractometer, and an arithmetic processing section for determining concentration of a component based on a detection signal obtained by the differential refractometer.

Effects of the Invention

The first measurement method of the present invention includes continuously stirring the inside of a mobile phase container, and thus, the composition of the mobile phase inside the mobile phase container is made uniform, and undulation of the detection signal is suppressed.

The "undulation" here refers to a state in which the refractive index is repeatedly increased and reduced over time and a wave (including periodic and non-periodic waves) is appearing in the baseline.

Further, the "drift" refers to a state in which the refractive index keeps increasing over time, or keeps being reduced over time, and is a state in which the amount of change in the refractive index per time-varying amount is not zero.

The second measurement method of the present invention includes calculating the amount of drift in a baseline of a detection signal before measurement of a sample is started, and adjusting the degree of degassing of the mobile phase according to the calculated amount of drift, and thus, measurement of a sample may be performed in a state in which the amount of drift in the baseline of a detection signal is controlled to within a desired target range, and the accuracy of measurement of a sample may be improved.

The first differential refractometer of the present invention includes a stirring mechanism for continuously stirring the inside of the mobile phase container, and thus, the composition of the mobile phase in the mobile phase container is made uniform, and undulation of the baseline of a detection signal is suppressed.

The second differential refractometer of the present invention includes a control section for capturing a detection signal obtained by the photodetector from the measurement section, and for controlling operation of the degassing device based on the detection signal, and the control section includes drift amount setting means for setting a target range of the amount of drift in a baseline of the detection signal of the photodetector, drift amount calculation means for calculating the amount of drift in the baseline of the detection signal before measurement of a sample is performed, and degassing degree control means for adjusting the degree of degassing of the mobile phase by the degassing device before measurement of the sample is performed, in such a way that the amount of drift calculated by the drift amount calculation means falls within the target range set by the drift amount setting means, and thus, the amount of drift in the baseline of a detection signal is controlled to within a desired target range before measurement of a sample is performed. The accuracy of measurement of a sample is thereby improved.

The liquid chromatograph of the present invention includes the differential refractometer of the present invention, and is capable of performing highly reliable quantitative analysis where undulation and a drift in the baseline of a detection signal are controlled.

EMBODIMENTS OF THE INVENTION

First Embodiment

Figure 1:
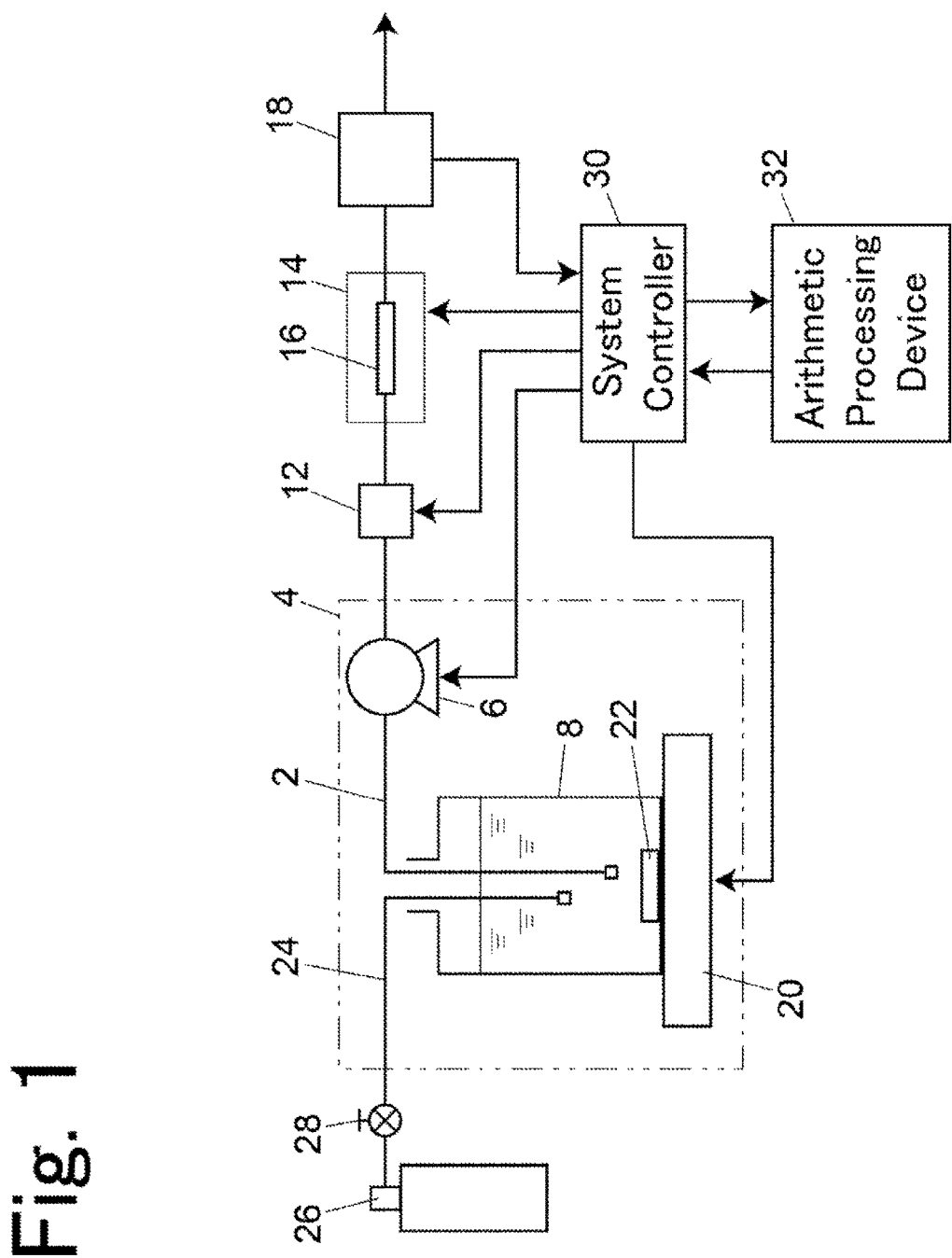
FIG. 1 is a schematic configuration diagram showing an embodiment of a liquid chromatograph including a differential refractometer.

An embodiment of a liquid chromatograph including a differential refractometer will be described with reference to FIG. 1.

The liquid chromatograph uses a differential refractometer as a detector for detecting a component separated by an analytical column 16. Details will be given later, but a measurement section 18 includes a measurement cell and an optical system. The measurement cell of the measurement section 18 includes a sample cell through which a sample is to pass together with a mobile phase, and a reference cell for a reference solution.

An analytical channel 2 serves also as a sample introduction channel for introducing a sample and a mobile phase into the sample cell. A mobile phase supply section 4 for delivering a mobile phase at the analytical channel 2 is provided. The mobile phase supply section 4 supplies a mobile phase contained in a mobile phase container 8 to the analytical channel 2 by a pump 6. A sample introduction section 12 and the analytical column 16 are provided on the analytical channel 2 in this order from the upstream side. The sample introduction section 12 is an autosampler for introducing a sample into the analytical channel 2, a sample introduced into the analytical channel 12 is introduced into the analytical column 16 by a mobile phase from the mobile phase supply section 4, and each component separated by the analytical column 16 flows through the sample cell of the measurement section 18 together with the mobile phase. The analytical column 16 is accommodated inside a column oven 14 whose internal temperature is maintained constant.

The inside of the mobile phase container 8 is to be stirred by a magnetic stirrer 20. The magnetic stirrer 20 is a stirring mechanism for remotely driving a stirrer 22 disposed inside the mobile phase container 8 by magnetic force. The composition of the mobile phase in the mobile phase container 8 is maintained uniform by evenly driving the stirrer 22.

A tube 24 from a helium tank 26 for supplying helium gas, which is a degassing gas, is inserted in the mobile phase container 8, and dissolved oxygen and the like are removed inside the mobile phase container 8. The amount of supply of helium gas from the helium tank 26 to the mobile phase container 8 is adjusted by a pressure adjustment valve 28. The pressure adjustment valve 28 is configured to control the pressure at the outlet of the helium tank 26 to a set pressure. The degree of opening of the outlet of the helium tank 26 is adjusted according to the pressure set at the pressure adjustment valve 28, and the amount of supply of helium gas is thereby adjusted. The pressure set at the pressure adjustment valve 28 is set by an analyst.

The helium tank 26 and the pressure adjustment valve 28 configure a degassing gas supply section. The degassing gas supply section realizes a degassing device for degassing a mobile phase in the mobile phase container 8, but the configuration of the degassing device is not limited thereto. For example, the dissolved oxygen inside the mobile phase container 8 may be suctioned and removed by a vacuum pump. In this case, the degree of degassing of a mobile phase in the mobile phase container 8 is changed by controlling the revolutions of the vacuum pump.

Operation of the pump 6, the autosampler 12, the column oven 14, and the magnetic stirrer 20 is controlled by an arithmetic processing device 32 through a system controller 30. The arithmetic processing device 32 is realized by a general-purpose personal computer or a dedicated computer, for example. Information such as an analysis schedule or an analysis condition is set at the arithmetic processing device 32, and signals based on these pieces of information are transmitted to the system controller 30. The system controller 30 controls operation of the pump 6, the autosampler 12, the column oven 14, and the magnetic stirrer 20 based on the signals provided by the arithmetic processing device 32.

Figure 2:
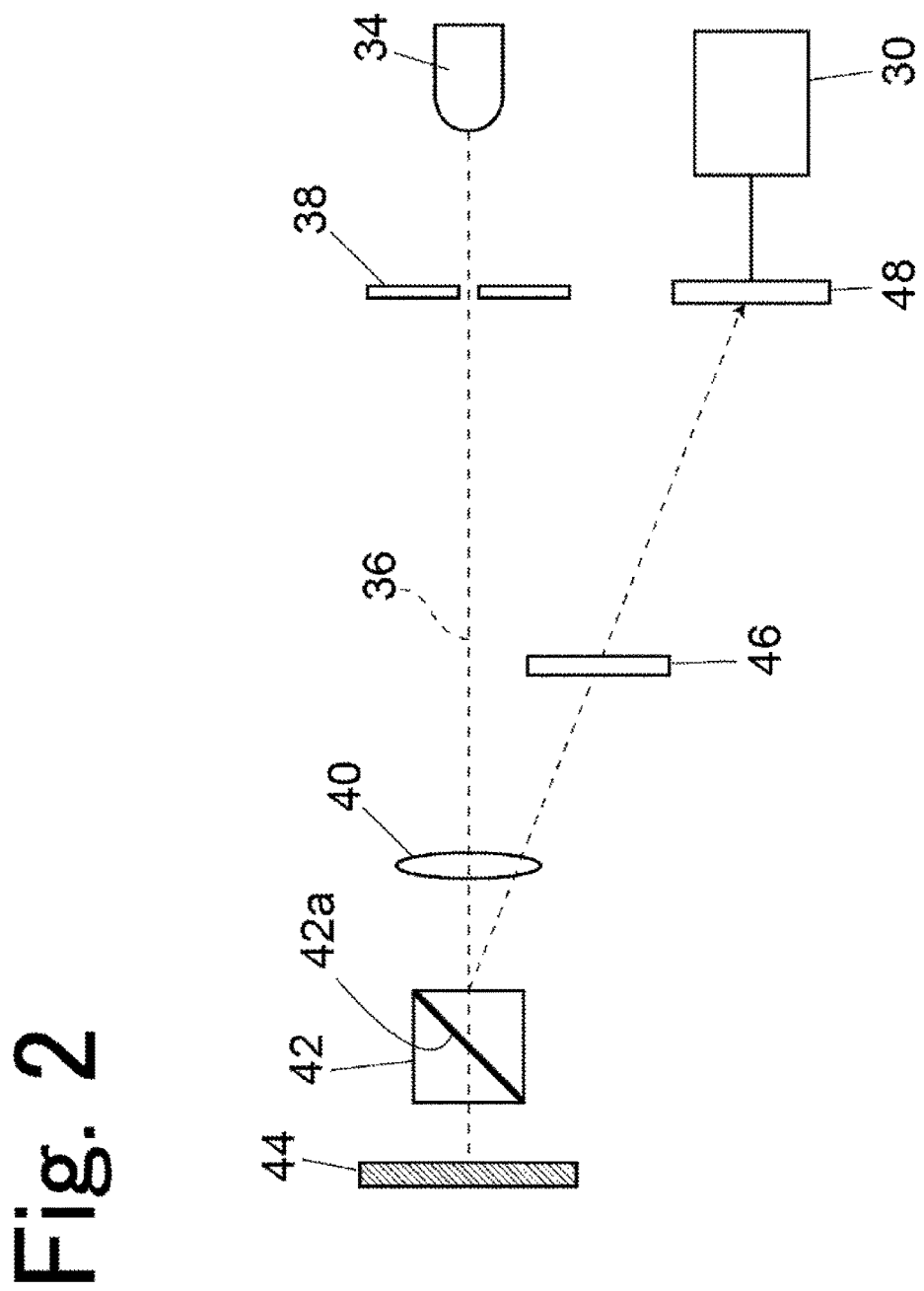
FIG. 2 is a diagram showing an optical system of the differential refractometer according to the present embodiment.

Now, an optical system of the measurement section 18 will be described with reference to FIG. 2.

A measurement cell 42 is disposed on the optical axis of light 36 from a light source 34 entering through a slit 38. As described above, the measurement cell 42 includes a sample cell through which a sample is to pass and a reference cell for a reference solution, and the two cells are separated by a partition wall 42a. A lens 40 is disposed on the side of the measurement cell 42 that is irradiated by the light 36 from the light source 34, and a mirror 44 is disposed on the opposite side from the lens 40 across the measurement cell 42. The measurement cell 42 is disposed in such a way that the light 36 diagonally enters the partition wall 42a. A light receiving element 48 is disposed on the optical path of light reflected by the mirror 44, and measurement light reflected by the mirror 44 and transmitted through the measurement cell 42 is to be imaged on the light receiving element 48. A zero glass 46 for moving a slit image on the light receiving element 48 in parallel is disposed on the optical path of light after reflection by the mirror 44, between the lens 40 and the light receiving element 48.

Figure 8:
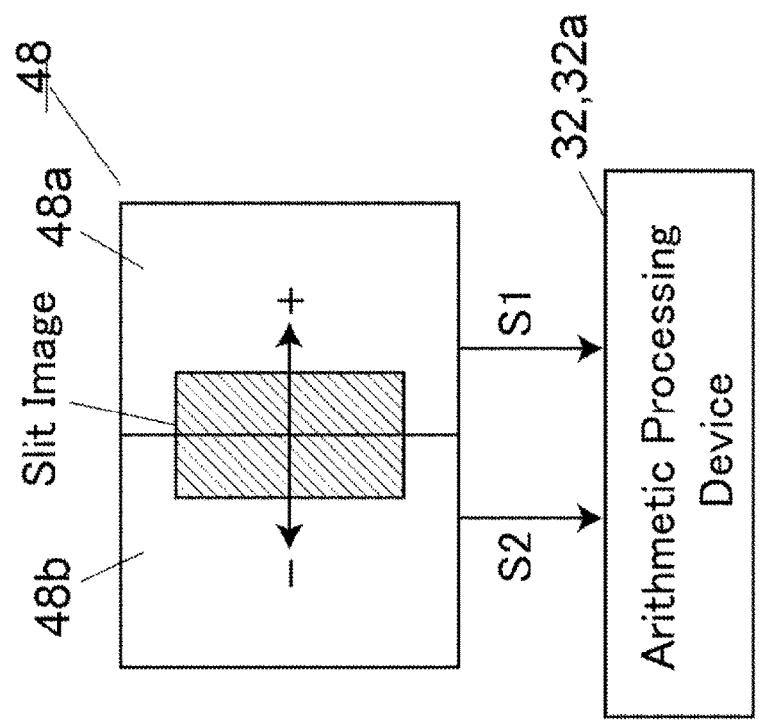
FIG. 8 is a conceptual diagram for describing a movement direction of a slit image formed on a detection element, and a signal that is output from the detection element.

An example of the optical system of the measurement section 18 is shown in FIG. 8. As shown in FIG. 8, the light receiving surface of the light receiving element 48 is divided into two light receiving areas 48a and 48b, and a slit image is formed across these light receiving areas 48a, 48b. The light receiving areas 48a and 48b are to output signals S1 and S2 according to respective amounts of incident light, and the signals S1 and S2 output from the light receiving areas 48a and 48b are to be captured by the arithmetic processing device 32 through the system controller 30.

A slit image formed on the light receiving element 48 is adjusted in such a way that, when the difference between a refractive index K1 of the sample cell of the measurement cell 42 and a refractive index K2 of the reference cell (K1−K2) is zero, the amount of incident light is the same between the light receiving areas 48a and 48b. Whereas the refractive index K2 of the reference cell of the measurement cell 42 is fixed, the refractive index K1 of the sample cell is changed according to the concentration of a sample component in the solution flowing through the sample cell, and thus, when the concentration of a sample component in the solution flowing through the sample cell changes, a refractive index difference (K1−K2) between the sample cell and the reference cell is changed. When the refractive index difference (K1−K2) between the sample cell and the reference cell is changed, the slit image is displaced toward the side of the light receiving area 48a or 48b, and the signals S1 and S2 output from the light receiving areas 48a and 48b are changed.

In the present embodiment, the direction of displacement of the slit image to the light receiving area 48a side is referred to as "+ (positive)", and the direction to the light receiving area 48b side is referred to as "− (negative)". When the refractive index K1 of the sample cell is increased (the refractive index difference (K1−K2) between the sample cell and the reference cell is increased), the slit image is displaced to the "+" side, and when the refractive index K1 of the sample cell is reduced (the refractive index difference (K1−K2) between the sample cell and the reference cell is reduced), the slit image is displaced to the "−" side.

An amount of displacement ΔL of the slit image formed on the light receiving element 48 is detected by, for example, the following formula:

$$\Delta L = (S1-S2)/(S1+S2)$$

The arithmetic processing device 32 has a function of calculating the ΔL above upon capturing of the signals S1 and S2, and of determining the concentration of a sample component in the solution flowing through the sample cell based on the calculated ΔL. The relationship between ΔL and the concentration of a sample component is set in advance, and is stored in the arithmetic processing device 32.

Referring back to FIG. 1, the mobile phase container 8 is to be continuously stirred by the magnetic stirrer 20, as described above. Depending on the amount of dissolved oxygen or the like, the composition of a mobile phase is sometimes not uniform inside the mobile phase container 8, and this may cause the refractive index of the sample cell of the measurement cell 42 to be changed over time, thereby causing undulation to occur in the baseline of a signal output from the light receiving element 48 of the measurement section 18.

Figure 3:
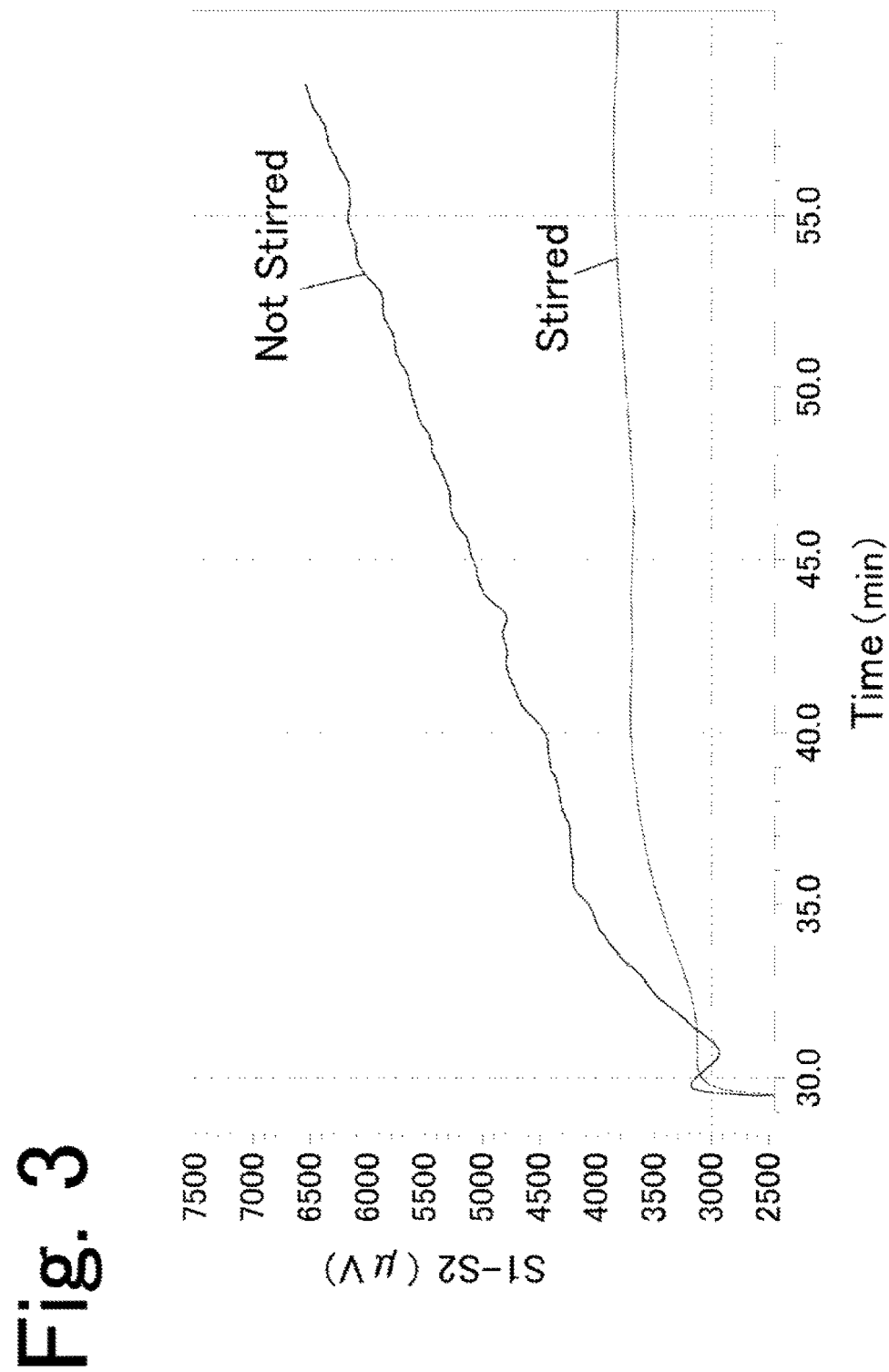
FIG. 3 is a diagram showing an example of the baseline of a detection signal when the inside of a mobile phase container is continuously stirred, and of the baseline of a detection signal when stirring is not performed.

FIG. 3 is a graph showing examples of a change over time in the difference (S1−S2) between detection signals of the light receiving areas 48a and 48b of the light receiving element 48 of the measurement section 18. In the measurement, only the mobile phase is made to flow without introduction of a sample into the analytical channel 2. One of the waveforms, "not stirred", is a waveform that is obtained when the operation of the magnetic stirrer 20 is stopped and the mobile phase is delivered without the inside of the mobile phase container 8 being stirred, and the other waveform, "stirred", is a waveform that is obtained when the mobile phase is delivered with the inside of the mobile phase container 8 being stirred by the magnetic stirrer 20.

As can be seen from the waveforms, there is undulation of the baseline when the inside of the mobile phase container 8 is not stirred, but the undulation is suppressed when delivery is performed while stirring the inside of the mobile phase container 8.

The stirring mechanism for stirring the inside of the mobile phase container 8 is not limited to the magnetic stirrer. Any mechanism may be used so long as the inside of the mobile phase container 8 may be stirred continuously.

Second Embodiment

Figure 4:
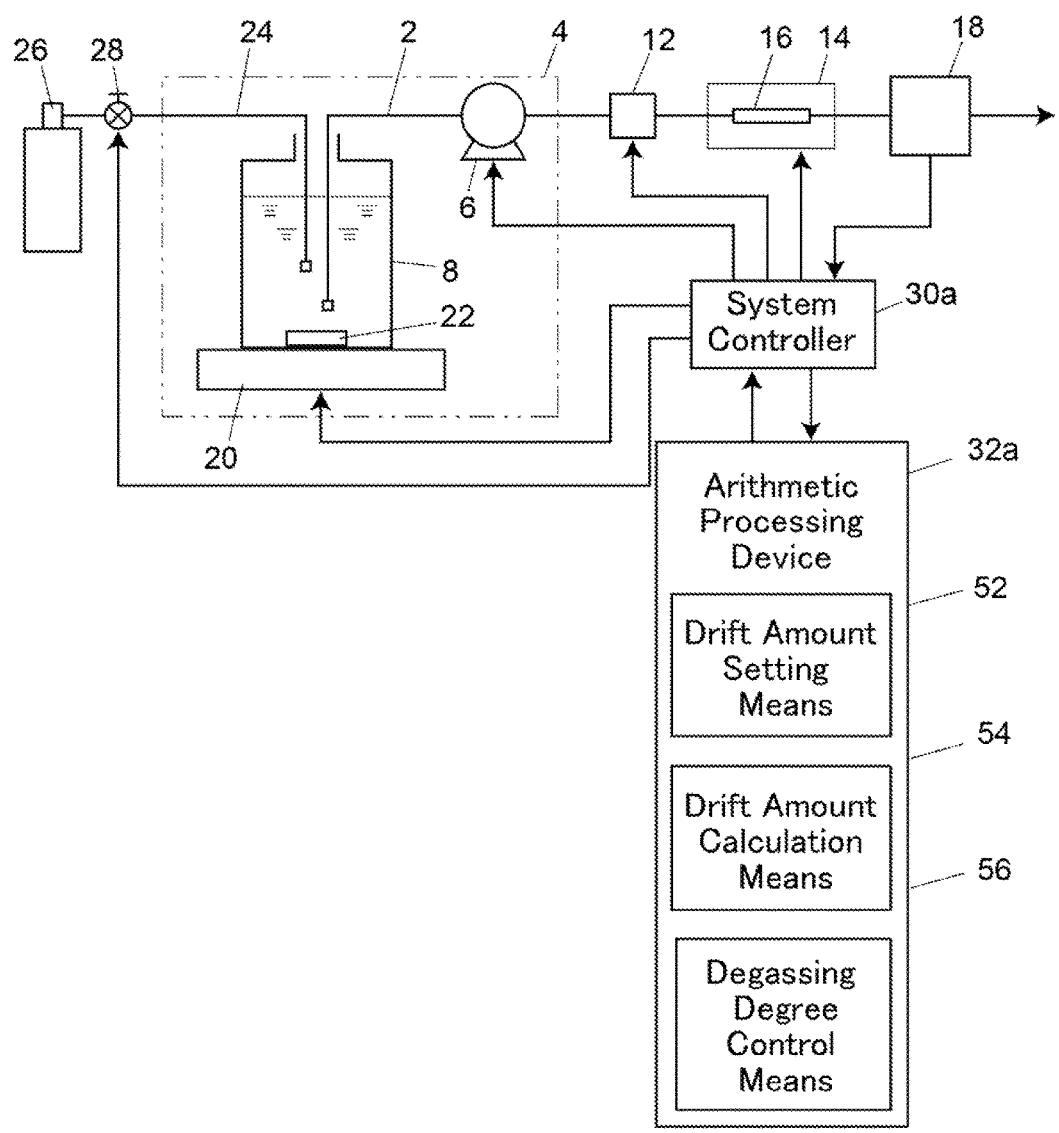
FIG. 4 is a schematic configuration diagram showing another embodiment of a liquid chromatograph including a differential refractometer.

Next, another embodiment of the liquid chromatograph including a differential refractometer will be described with reference to FIG. 4.

Figure 7:
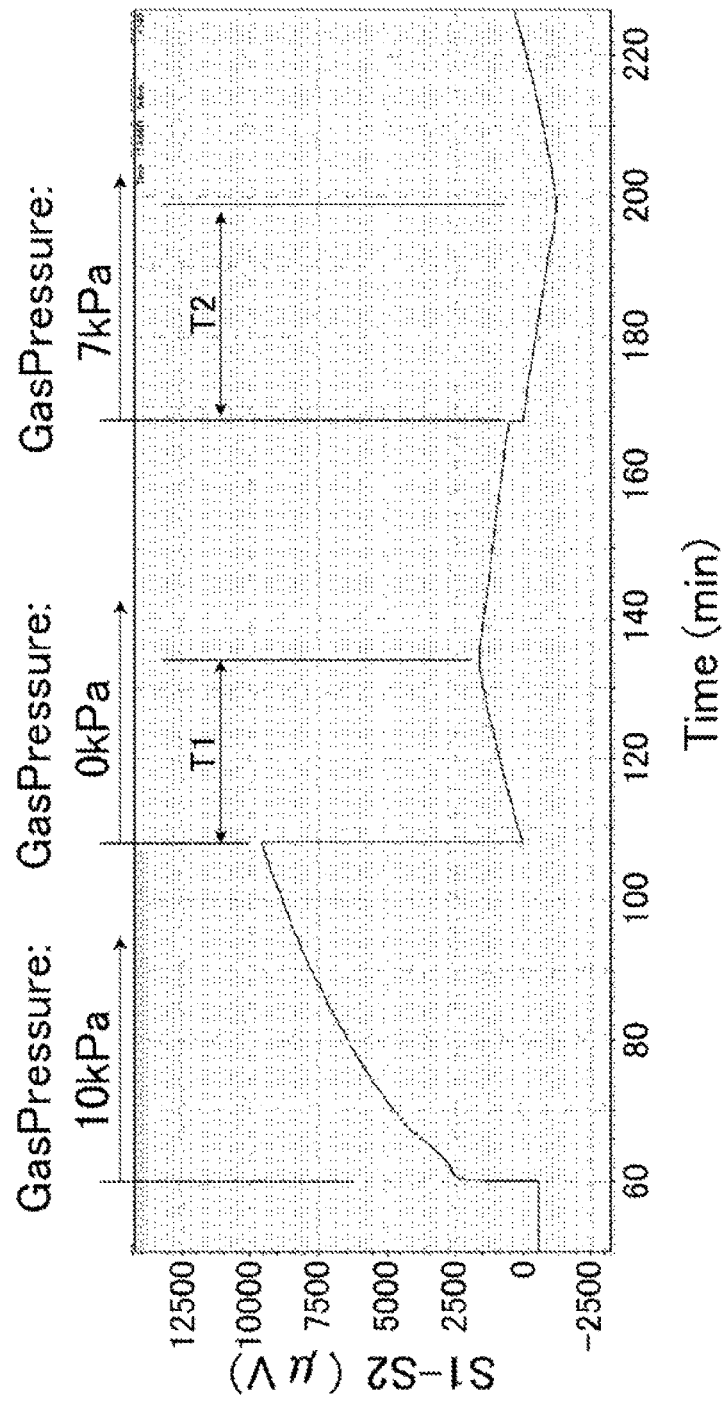
FIG. 7 is a diagram showing the baseline of a detection signal, showing a change in the amount of drift when the amount of supply of degassing gas is changed.

The second embodiment is different from the first embodiment described above in that the set pressure of a pressure adjustment valve 28 for controlling the amount of supply of degassing gas to be supplied into a mobile phase container 8 is automatically set by the device. A system controller 30a controls a pump 6, a sample introduction section 12, a column oven 14, a magnetic stirrer 20, and the pressure adjustment valve 28 based on signals from an arithmetic processing device 32a. As is the arithmetic processing device 32 of the first embodiment, the arithmetic processing device 32a is realized by a general-purpose computer or a dedicated computer, for example. Output signals S1 and S2 (see FIG. 7) from a light receiving element 48 of a measurement section 18 are captured by the arithmetic processing device 32a through the system controller 30a. The arithmetic processing device 32a has a function of determining the concentration of a sample component based on the captured signals S1 and S2.

The arithmetic processing device 32a further includes drift amount setting means 52, drift amount calculation means 54, and degassing degree control means 56. These means 52, 54, and 56 are provided to adjust the amount of supply of degassing gas to be supplied to the mobile phase container 8 and to adjust the dissolved oxygen concentration in the mobile phase flowing through the sample cell in such a way that the amount of drift in the baseline of a detection signal obtained by the detection section 18 comes closer to the amount of drift set by the analyst. These means 52, 54, and 56 are functions that are realized by programs stored in the arithmetic processing device 32a and an arithmetic device such as a CPU for executing the programs.

The drift amount setting means 52 is configured to perform setting by allowing an analyst to input a target range of the amount of drift. The drift amount calculation means 54 is configured to calculate the amount of drift per unit time (for example, RIU/min) based on the output signals S1 and S2 of light receiving areas 48a and 49b (see FIG. 7) captured through the system controller 30a. The amount of drift ΔD [μRIU/min] is a change in the refractive index per arbitrary time, and may be determined by, for example, the following formula: Additionally, t refers to time (min).

$$\Delta D = (S1-S2)/t$$

The amount of drift ΔD is of a case where the set polarity (output polarity) of the differential refractometer is positive. In the case where the set polarity is negative, the sign of the value of the amount of drift ΔD will be opposite that of the case where the set polarity is positive. An analyst can set the polarity of the differential refractometer in, for example, the system controller 30a through the arithmetic processing device 32a.

The degassing degree control means 56 is configured to adjust the set pressure of the pressure adjustment valve 28 in such a way that the amount of drift calculated by the drift amount calculation means 54 comes closer to the target range of the amount of drift set by the drift amount setting means 52.

Figure 6:
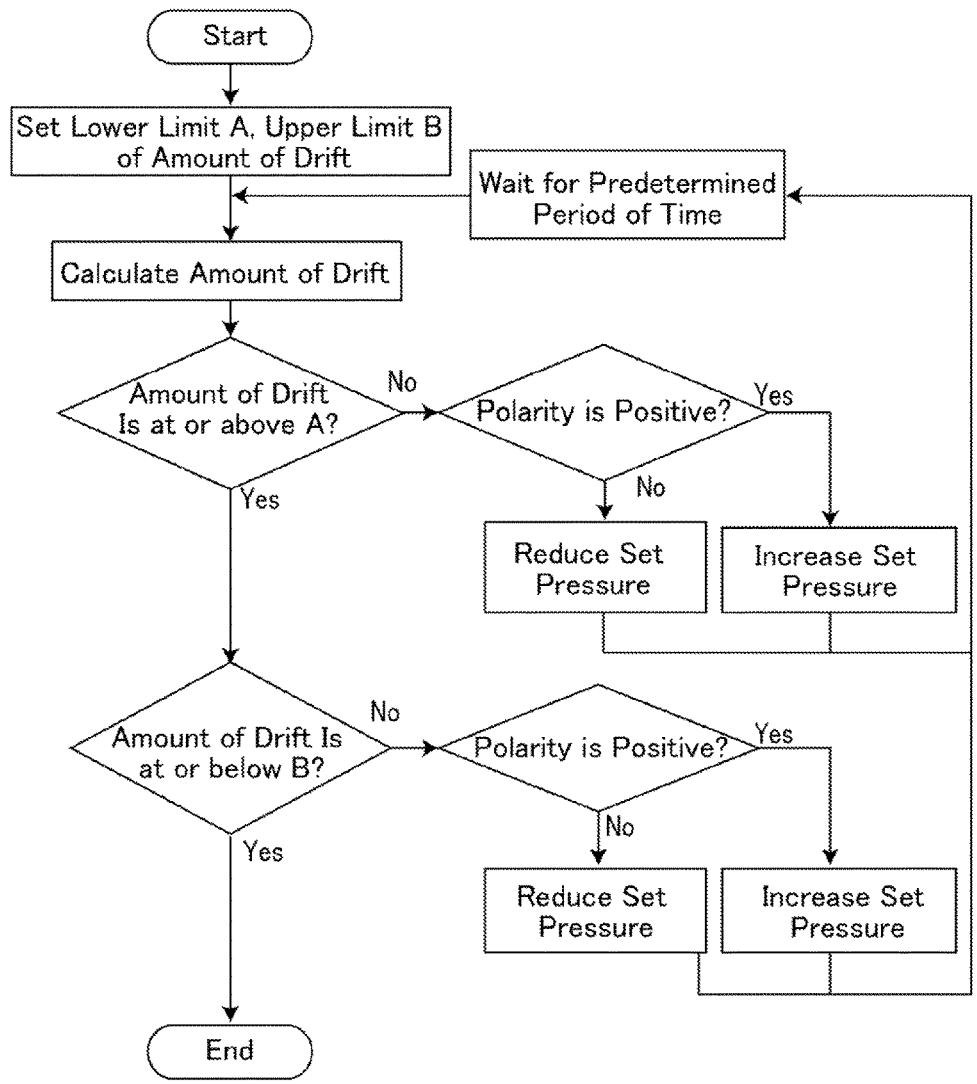
FIG. 6 is a flow chart showing operation of adjusting the amount of drift according to the present embodiment.

FIG. 6 is a graph showing the relationship between the amount of supply (gas pressure) of a degassing gas (helium gas) supplied to the mobile phase container 8 and the output signal difference S1−S2 (see FIG. 7) between one of the light receiving areas 48a and 48b of the light receiving element 48 of the measurement section 18. The gas pressure refers to the set pressure of the pressure adjustment valve 28.

When the set pressure (gas pressure) is 10 kPa, the signal intensity increases greatly over time, and the baseline of the output signal difference S1−S2 is drifted to the positive side. Then, when the set pressure (gas pressure) is changed to 0 kPa, the amount of drift is gradually reduced, and is finally changed to the negative side. Further, when the set pressure (gas pressure) is changed to 7 kPa, the amount of drift in the baseline is gradually increased, and the direction of the drift is finally changed to the positive side. Additionally, in this data, since zero adjustment is performed for the detector at around 108 minutes, the signal intensity is displayed as being drastically reduced.

It can be understood from the description given above that the amount and direction of drift in the baseline of a detection signal can be controlled by adjusting the amount of supply of degassing gas to the mobile phase container 8. Additionally, times T1 and T2 after the set pressure (gas pressure) of the pressure adjustment valve 28 is changed and until the direction of drift is changed are delay times required for the mobile phase in the mobile phase container 8 whose degree of degassing has been changed to reach the sample cell.

Figure 5:
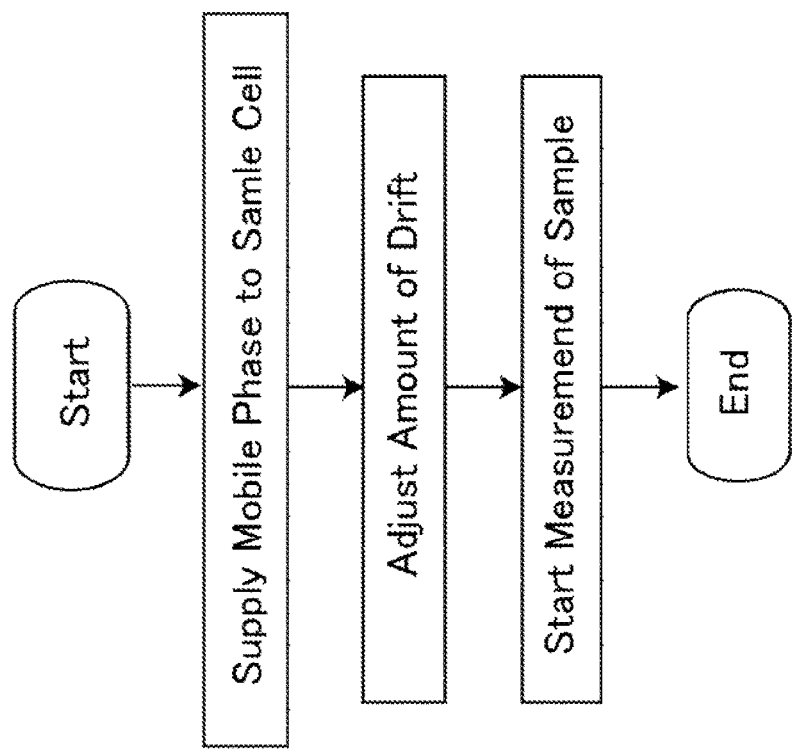
FIG. 5 is a flow chart showing measurement operation according to the present embodiment.

A measurement operation of the present embodiment will be described with reference to FIG. 4 and the flow chart in FIG. 5.

A mobile phase is supplied from the mobile phase supply section 4 to the sample cell. Before starting measurement of a sample, the amount of drift in the baseline of a detection signal of the detection section 18 is adjusted. Adjustment of the amount of drift will be described later in detail. When the amount of drift in the baseline of a detection signal is adjusted to a set target range, a sample is introduced into the analytical channel 2 by the sample introduction section 12 and measurement of the sample is performed while maintaining the pressure adjustment valve 28 in the above state.

Next, adjustment of the amount of drift in the baseline of a detection signal will be described with reference to FIG. 4 and the flow chart in FIG. 6.

First, when the stage of adjustment of the amount of drift is reached, the drift amount setting means 52 performs display on, for example, an external PC monitor or a dedicated monitor provided to the device to urge the analyst to input the target range of the amount of drift. The target range of the amount of drift set at this time includes, for example, an upper limit A and a lower limit B. Values of A and B input by the analyst are set as the target range of the amount of drift, and are used to control the set pressure of the pressure adjustment valve 28 by the degassing degree control means 56.

After the target range of the amount of drift is set, the drift amount calculation means 54 calculates the amount of drift based on a detection signal of the measurement section 18. The degassing degree control means 56 determines whether the amount of drift calculated by the drift amount calculation means 54 is within the lower limit A and the upper limit B which have been set, and adjusts the set pressure of the pressure adjustment valve 28 in such a way that the amount of supply of degassing gas is increased or decreased according to the result.

In the case where the amount of drift is below the lower limit A, if the polarity of the device is set to positive, the set pressure of the pressure adjustment valve 28 is increased so that the amount of supply of degassing gas is increased. On the other hand, if the polarity of the device is set to negative, the set pressure of the pressure adjustment valve 28 is reduced so that the amount of supply of degassing gas is reduced.

In the case where the amount of drift is above the upper limit B, if the polarity of the device is set to positive, the set pressure of the pressure adjustment valve 28 is reduced so that the amount of supply of degassing gas is reduced. On the other hand, if the polarity of the device is set to negative, the set pressure of the pressure adjustment valve 28 is increased so that the amount of supply of degassing gas is increased.

The range of adjustment of the set pressure of the pressure adjustment valve 28 is determined according to the size of the difference between the amount of drift calculated by the drift amount calculation means 54 and the lower limit A or the upper limit B. Further, since the rate of replacement of dissolved oxygen in the mobile phase by helium varies depending on the remaining amount of mobile phase in the mobile phase container 8, the range of adjustment of the set pressure of the pressure adjustment valve 28 is determined according to the remaining amount of mobile phase in the mobile phase container 8. The degassing degree control means 56 of the arithmetic processing device 32a takes the difference between the amount of drift and the lower limit A or the upper limit B, and the remaining amount of mobile phase as parameters, and stores data of the range of adjustment for the pressure adjustment valve 28 prepared according to each parameter, and the set pressure of the pressure adjustment valve 28 is adjusted based on the data.

After waiting is performed for a predetermined period of time after such adjustment is performed and until the influence of the adjustment is reflected in the detection signal, the amount of immediate drift is calculated by the drift amount calculation means 54, and the set pressure of the pressure adjustment valve 28 is adjusted based on the calculation result. The set pressure of the pressure adjustment valve 28 adjusted at this time is maintained at least during measurement of a sample that is performed after the adjustment.

DESCRIPTION OF REFERENCE SIGNS

2: Analytical channel (sample introduction channel)
4: Mobile phase supply section
6: Pump
8: Mobile phase container
12: Sample introduction section
14: Column oven
16: Analytical column
18: Measurement section
20: Magnetic stirrer
22: Stirrer
24: Tube
26: Helium tank
28: Pressure adjustment valve
30, 30a: System controller
32, 32a: Arithmetic processing device
52: Drift amount setting means
54: Drift amount calculation means
56: Degassing degree control means

The invention claimed is:

1. A measurement method using a differential refractometer including a sample cell through which a sample solution is to pass, a reference cell for a reference solution, and an optical system configured to radiate light that is sequentially transmitted through both of the sample cell and the reference cell and to detect transmitted light by a photodetector, the differential refractometer being for measuring a refractive index difference between the sample cell and the reference cell by detecting displacement of light which has been transmitted through the sample cell and the reference cell, the measurement method comprising:
   supplying a mobile phase to the sample cell;
   degassing the mobile phase to be supplied to the sample cell;
   calculating an amount of drift in a baseline of a detection signal of the photodetector before measurement of a sample is started;
   adjusting a degree of degassing of the mobile phase so that the calculated amount of drift falls within a predetermined range;
   injecting a sample into the channel through which the mobile phase is flowing, after adjustment of the degree of degassing of the mobile phase;
   radiating light on the sample cell and the reference cell and detecting transmitted light by the photodetector; and
   determining the refractive index difference between the sample cell and the reference cell based on a detection signal of the photodetector.

2. The measurement method according to claim 1, wherein degassing of the mobile phase is performed by supplying a degassing gas to a mobile phase container containing the mobile phase, and change of the degree of degassing of the mobile phase is performed by adjusting an amount of supply of the degassing gas to the mobile phase container.

3. The measurement method according to claim 1,
   wherein, in a case where a refractive index of the sample cell is given as K1 and a refractive index of the reference cell is given as K2, a direction regarding a drift in a baseline of a detection signal of the photodetector of increase in a refractive index difference (K1−K2) between the sample cell and the reference cell is given as a positive direction, and the direction of reduction in the refractive index difference (K1−K2) between the sample cell and the reference cell is given as a negative direction,
   in the adjusting a degree of degassing of the mobile phase, the degree of degassing of the mobile phase is increased to increase the amount of drift in the baseline of the detection signal of the photodetector, and the degree of degassing of the mobile phase is reduced to reduce the amount of drift.

4. A differential refractometer comprising:
   a measurement cell including a sample cell through which a sample solution is to pass, and a reference cell for a reference solution;
   a sample introduction channel, connected to the sample cell, for introducing a sample into the sample cell together with a mobile phase;
   a measurement section including a light source for radiating light toward the measurement cell, and a photodetector for detecting light which has passed through the sample cell and the reference cell;
   a mobile phase supply section, including a mobile phase container for containing a mobile phase, for supplying the mobile phase to the sample cell through the sample introduction channel;
   a degassing device for degassing the mobile phase inside the mobile phase container; and
   a control section for capturing a detection signal obtained by the photodetector from the measurement section, and for controlling operation of the degassing device based on the detection signal,
   wherein the control section includes drift amount setting means for setting a target range of an amount of drift in a baseline of the detection signal of the photodetector, drift amount calculation means for calculating the amount of drift in the baseline of the detection signal before measurement of a sample is performed, and degassing degree control means for adjusting a degree of degassing of the mobile phase by the degassing device before measurement of the sample is performed, in such a way that the amount of drift calculated by the drift amount calculation means falls within the target range set by the drift amount setting means.

5. The differential refractometer according to claim 4, wherein the degassing device is a degassing gas supply section including a supply source for supplying a degassing gas into the mobile phase container, and an adjustment mechanism for variably adjusting an amount of supply.

6. The differential refractometer according to claim 5, wherein the degassing gas is helium gas.

7. The differential refractometer according to claim 4, wherein, in a case where a refractive index of the sample cell is given as K1 and a refractive index of the reference cell is given as K2, a direction regarding a drift in a baseline of a detection signal of the photodetector of increase in a refractive index difference (K1−K2) between the sample cell and the reference cell is given as a positive direction, and the direction of reduction in the refractive index difference (K1−K2) between the sample cell and the reference cell is given as a negative direction, the degassing degree control means increases the degree of degassing of the mobile phase if the amount of drift calculated by the drift amount calculation means is lower than the target range, and reduces the degree of degassing of the mobile phase if the amount of drift calculated by the drift amount calculation means is higher than the target range.

8. A liquid chromatograph comprising:

a differential refractometer;

a sample introduction section for introducing a sample into a sample introduction channel of the differential refractometer;

an analytical column for separating a sample into components, provided on the sample introduction channel, on an upstream side of the differential refractometer; and an arithmetic processing section for determining concentration of a component based on a detection signal obtained by the differential refractometer, wherein the differential refractometer comprising:

a measurement cell including a sample cell through which a sample solution is to pass, and a reference cell for a reference solution;

a sample introduction channel, connected to the sample cell, for introducing a sample into the sample cell together with a mobile phase;

a measurement section including a light source for radiating light toward the measurement cell, and a photodetector for detecting light which has passed through the sample cell and the reference cell;

a mobile phase supply section, including a mobile phase container for containing a mobile phase, for supplying the mobile phase to the sample cell through the sample introduction channel;

a degassing device for degassing the mobile phase inside the mobile phase container; and a control section for capturing a detection signal obtained by the photodetector from the measurement section, and for controlling operation of the degassing device based on the detection signal, and wherein the control section includes drift amount setting means for setting a target range of an amount of drift in a baseline of the detection signal of the photodetector, drift amount calculation means for calculating the amount of drift in the baseline of the detection signal before measurement of a sample is performed, and degassing degree control means for adjusting a degree of degassing of the mobile phase by the degassing device before measurement of the sample is performed, in such a way that the amount of drift calculated by the drift amount calculation means falls within the target range set by the drift amount setting means.

9. The liquid chromatograph according to claim 8, wherein the degassing device is a degassing gas supply section including a supply source for supplying a degassing gas into the mobile phase container, and an adjustment mechanism for variably adjusting an amount of supply.

10. The liquid chromatograph according to claim 8, wherein, in a case where a refractive index of the sample cell is given as K1 and a refractive index of the reference cell is given as K2, a direction regarding a drift in a baseline of a detection signal of the photodetector of increase in a refractive index difference (K1−K2) between the sample cell and the reference cell is given as a positive direction, and the direction of reduction in the refractive index difference (K1−K2) between the sample cell and the reference cell is given as a negative direction, the degassing degree control means increases the degree of degassing of the mobile phase if the amount of drift calculated by the drift amount calculation means is lower than the target range, and reduces the degree of degassing of the mobile phase if the amount of drift calculated by the drift amount calculation means is higher than the target range.

\* \* \* \* \*